(12) United States Patent
Samuels

(10) Patent No.: US 6,588,588 B2
(45) Date of Patent: Jul. 8, 2003

(54) MEDICAL GUIDEWIRE ADAPTER FOR PACKAGING REUSE

(76) Inventor: Shaun L. W. Samuels, 1055 Sonoma Ave., Menlo Park, CA (US) 94025

( * ) Notice: Subject to any disclaimer, the term of this patent is extended or adjusted under 35 U.S.C. 154(b) by 0 days.

(21) Appl. No.: 09/832,173

(22) Filed: Apr. 10, 2001

(65) Prior Publication Data

US 2002/0144920 A1 Oct. 10, 2002

(51) Int. Cl.$^7$ ................................................ B65D 83/10
(52) U.S. Cl. ........................ 206/364; 206/438; 206/804; 604/284
(58) Field of Search ................................ 206/364, 804, 206/370, 702, 438, 63.3, 389, 315.6, 227, 225, 363; 600/585; 604/284, 264, 256, 171; 285/131.1, 132.1

(56) References Cited

U.S. PATENT DOCUMENTS

| | | | |
|---|---|---|---|
| 156,586 A | 11/1874 | McNeil | |
| 385,937 A | 7/1888 | Lee | |
| 539,654 A | 5/1895 | Stewart | |
| 1,780,802 A | 11/1930 | Sutcliffe | |
| 1,816,301 A | 7/1931 | Sundell | |
| 1,926,836 A | 9/1933 | Corlett | |
| 2,920,394 A | 1/1960 | Soderbergh | |
| 3,326,551 A | * 6/1967 | Clarke | .......................... 482/81 |
| 3,633,758 A | 1/1972 | Morse et al. | |
| 3,902,679 A | 9/1975 | Bost | |
| 4,017,046 A | 4/1977 | Hicks | |
| 4,155,387 A | 5/1979 | Costa | |
| 4,193,699 A | 3/1980 | Haygeman et al. | |
| 4,600,100 A | 7/1986 | Solheim | |
| 4,617,693 A | * 10/1986 | Meyer et al. | ............. 15/104.33 |
| 4,668,225 A | * 5/1987 | Russo et al. | ................. 604/104 |
| 4,781,704 A | * 11/1988 | Potter | ........................... 604/105 |
| 4,997,084 A | 3/1991 | Opie et al. | |

(List continued on next page.)

Primary Examiner—J. Mohandesi
(74) Attorney, Agent, or Firm—Piper Rudnick

(57) ABSTRACT

An adapter that converts medical guidewire packaging into a reusable storage device. The adapter includes a conduit with first and second ends each having an opening and a passage there between. The adapter also includes an angled funnel with a duct and an enlarged end having an enlarged opening or port. The funnel is attached to the conduit between its ends and the duct of the funnel is in communication with the passage of the conduit. The first end of the conduit of the adapter is inserted into the opening of one end of a packaging tube while the other end of the packaging tube is inserted into the opening of the second end of the conduit of the adapter. Medical guidewires are inserted into the conduit of the adapter via the funnel and guided into the packaging tube by the funnel's duct and the adapter's conduit.

8 Claims, 2 Drawing Sheets

U.S. PATENT DOCUMENTS

| | | | |
|---|---|---|---|
| 5,102,399 A | | 4/1992 | Chu |
| 5,117,839 A | * | 6/1992 | Dance .................. 600/434 |
| 5,125,416 A | | 6/1992 | Phillips |
| 5,323,992 A | | 6/1994 | Sifers et al. |
| 5,339,833 A | | 8/1994 | Berthiaume et al. |
| 5,344,011 A | * | 9/1994 | DiBernardo et al. ........ 206/364 |
| 5,429,268 A | | 7/1995 | Hale et al. |
| 5,472,081 A | | 12/1995 | Kilgrow et al. |
| 5,503,266 A | | 4/1996 | Kalbfeld et al. |
| 5,507,300 A | | 4/1996 | Mukai et al. |
| 5,535,745 A | | 7/1996 | Ingram et al. |
| 5,575,382 A | | 11/1996 | Sobel et al. |
| 5,609,311 A | | 3/1997 | Palm |
| 5,611,428 A | | 3/1997 | Banerian |
| 5,720,301 A | | 2/1998 | Van't Hooft |
| 5,769,219 A | | 6/1998 | Shimel |
| 5,895,309 A | * | 4/1999 | Spector .................. 446/220 |
| 5,910,289 A | | 6/1999 | Sagstetter |
| 6,010,480 A | | 1/2000 | Abele et al. |
| 6,023,915 A | | 2/2000 | Colombo |
| 6,047,825 A | | 4/2000 | Samuels |
| 6,093,179 A | * | 7/2000 | O'Hara et al. .............. 604/159 |
| 6,110,146 A | | 8/2000 | Berthiaume et al. |
| 6,182,930 B1 | | 2/2001 | Lindborg |
| 6,258,072 B1 | * | 7/2001 | Weinberger .................. 604/256 |
| 6,375,006 B1 | * | 4/2002 | Samuels .................. 206/210 |
| 6,391,002 B1 | * | 5/2002 | Kokish .................. 604/103.06 |

* cited by examiner

MEDICAL GUIDEWIRE ADAPTER FOR PACKAGING REUSE

BACKGROUND OF THE INVENTION

The invention relates generally to systems for storing medical guidewires, and, more particularly, to an adapter for reinserting medical guidewires into the original packaging.

A number of interventional radiologic medical techniques have been recently developed to address a variety of potentially life-threatening human aliments. For example, interventional radiologic techniques have been developed to allow removal and/or destruction of stones in the biliary or excretory systems, blood clots in blood vessels and foreign bodies introduced by surgery that have migrated or become dysfunctional. As another example, interventional radiologic techniques may be utilized to treat stenosis, a degenerative blood vessel condition that causes a narrowing or constriction of the lumen so that blood flow is restricted. Due to their minimally invasive nature, interventional radiologic techniques provide an attractive alternative to surgery and thus have become very popular.

Interventional radiologic techniques typically utilize a wire that passes from outside of the patient's body, through his or her skin and into the tubular structure of interest. Once the wire is positioned in the desired location, medical devices such as catheters may be passed over the wire and thereby guided into the tubular structure so that the desired medical procedure may be performed. These "guidewires" as they have become to be called are of various lengths calibers and materials depending on the use for which they are intended.

In use, guidewires, after removal from their sterile packaging, are inserted into the patient and the portion remaining outside of the patient's body is spooled by hand as would be an extension cord. More specifically, the external portion of a guidewire is wound about itself in such a way as to lock the wire from springing into its naturally straight configuration. The wound portion of the guidewire is then placed into a large bowl containing a sterile saline solution so as to keep the wire wet. The saline solution also promotes the dissolution of any clots which may have formed on the guidewire after it is removed from the patient and placed in the bowl.

Wound guidewires also have a tendency to straighten once unlocked. As a result, a guidewire may spring open unexpectedly when it is being unwound during a procedure. When this occurs, the guidewire may inadvertently come into contact with non-sterile areas of the procedure room and hence need to be resterilized or completely replaced.

The bowls containing the wound guidewire portions and catheters may also be accidently tipped over during procedures. Such a scenario would also likely result in the catheters and guidewires coming into contact with non-sterile areas of the procedure room such as the floor.

U.S. Pat. No. 5,125,416 to Phillips discloses a rigid pipe that is coiled for storing medical guidewires. The rigid pipe stores the medical guidewires in a liquid solution that sterilizes the wires. Thus, the rigid pipe prevents the guidewires from contacting any non-sterile portion of the procedure room. The rigid pipe is capable of storing medical guidewires of various sizes and types. The rigid pipe includes a nozzle to allow guidewires to be inserted into the rigid pipe. This device, however, represents an additional, albeit minimal, cost in addition to the purchase price of the guidewires.

Medical guidewires typically are packaged in a single hoop tube. A separate bridge connects each end of the tube to form a closed loop. The single hoop tube includes a tiny hole in the side of the tubing. A tip of the medical guidewire protrudes from the hole so that the guidewire may be removed. In order to avoid the extra cost of the device of the Phillips '416 patent, and the disadvantages of the other prior art, it is desirable for medical guidewires to be reinserted into the packaging for storage and reuse. In current single hoop packaging, the user would have to try to reinsert the guidewire into the tiny hole in the side of the tubing. This process is time consuming and difficult. As a result, the medical guidewires and packaging tubes are only used once.

Accordingly, it is an object of the present invention to provide a reusable adapter that enables a user to recycle medical guidewire packaging.

It is another object of the present invention to provide an inexpensive adapter that may be removably inserted in packaging tubes to allow medical guidewires to be reinserted into the packaging.

SUMMARY OF THE INVENTION

The present invention is directed to an adapter that converts medical guidewire packaging tubes into reusable storage devices. The adapter includes a conduit with a first end having an opening, a second end having an opening and a passage extending there between. The adapter also includes a funnel with an enlarged end having a port that is in communication with a duct. The funnel is positioned between the ends of the conduit and the duct of the funnel is in communication with the passage of the conduit. The funnel duct is angled with respect to the passage of the conduit to facilitate removal and insertion of guidewires from and into a packaging tube. The first end of the conduit is sized so that it may be inserted into the opening of the packaging tube's leading end. The opening of the second end of the conduit is sized to receive the packaging tubes's trailing end. A medical guide wire is inserted in the conduit of the adapter via the duct of the funnel and guided into the packaging tube by the adapter's passage.

The following detailed description of embodiments of the invention, taken in conjunction with the appended claims and accompanying drawings, provide a more complete understanding of the nature and scope of the invention.

DESCRIPTION OF THE PREFERRED EMBODIMENT

Figure 1:
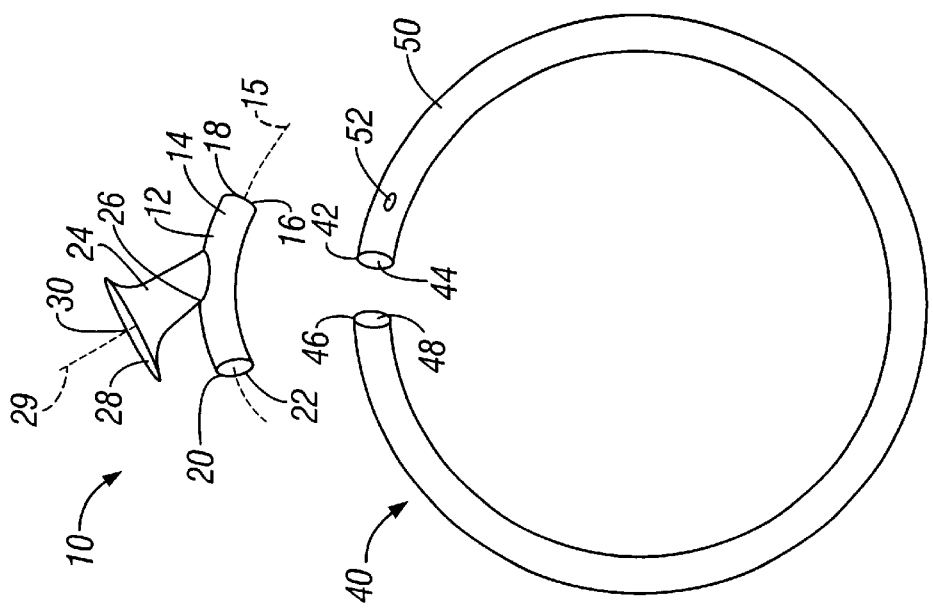
FIG. 1 is a perspective view of a single hoop packaging tube and an embodiment of the adapter of the present invention.

With reference to FIG. 1, the adapter of the present invention is indicated in general at 10. The adapter 10 preferably is constructed as a single piece out of an inexpensive, slightly flexible and durable material such as plastic. The adapter 10 includes a conduit 12 with a first end 16 having an opening 18, a second end 20 having an opening 22 and a passage 14 extending between the first end opening 18 and the second end opening 22.

FIG. 1 also illustrates a typical single hoop packaging tube 40 for medical guidewires. The single hoop packaging tube includes a leading end 42 with a leading opening 44, a trailing end 46 with a trailing opening 48 and a passageway 50 there between. Generally, the packaging tube is made from, but not limited to, polyethylene. The packaging tube 40 is typically shipped with a tubular connector (not shown) that joins leading end 42 to trailing end 46. The single hoop packaging tube 40 typically includes a tiny hole 52 positioned along the side of the tubing. During a medical procedure, medical guidewires are removed from the packing tube through the tiny hole 52.

Figure 2:
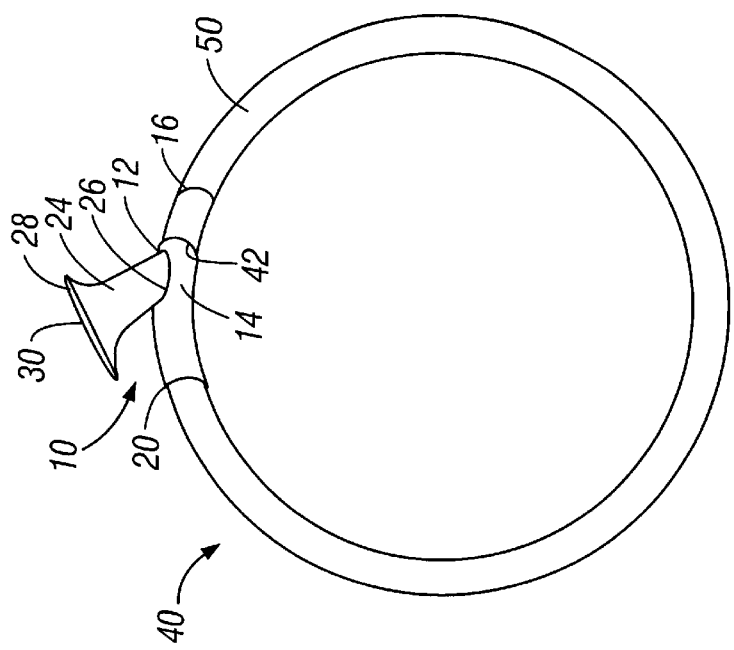
FIG. 2 is a perspective view of the adapter of FIG. 1 installed upon the single hoop packaging tube of FIG. 1 so that the packaging tube is converted for reuse.

The first end 16 of the adapter 10 is preferably smaller than the adapter's 10 second end 20. As illustrated in FIG. 2, the smaller first end 16 of the adapter 10 is sized to be inserted into opening 44 of leading end 42 of the packaging tube 40 while the larger second end 20, and corresponding larger opening 22, of the adapter 10 is sized to receive the trailing end 46 of a packaging tube 40. The openings 18 and 22 and ends 16 and 20, respectively, of the adapter 10 can be constructed in a variety of sizes to accommodate various sized packaging tubes.

The adapter 10 also includes a funnel 24 that is joined to the conduit 12 between the conduit ends 16 and 20. The funnel 24 includes a duct 26. The duct 26 of the funnel 24 is in communication with the passage 14 of the conduit 12. The funnel 24 includes an enlarged end 28 with an enlarged opening or port 30. Port 30 of enlarged end 28 is configured to receive single or multiple guidewires of various sizes. The longitudinal axis 29 of duct 26 of the funnel 24 preferably forms an angle of less than 90 degrees with the longitudinal axis 15 of the conduit passage 14 to facilitate removal and insertion of guidewires in the packaging tube 40.

Figure 3:
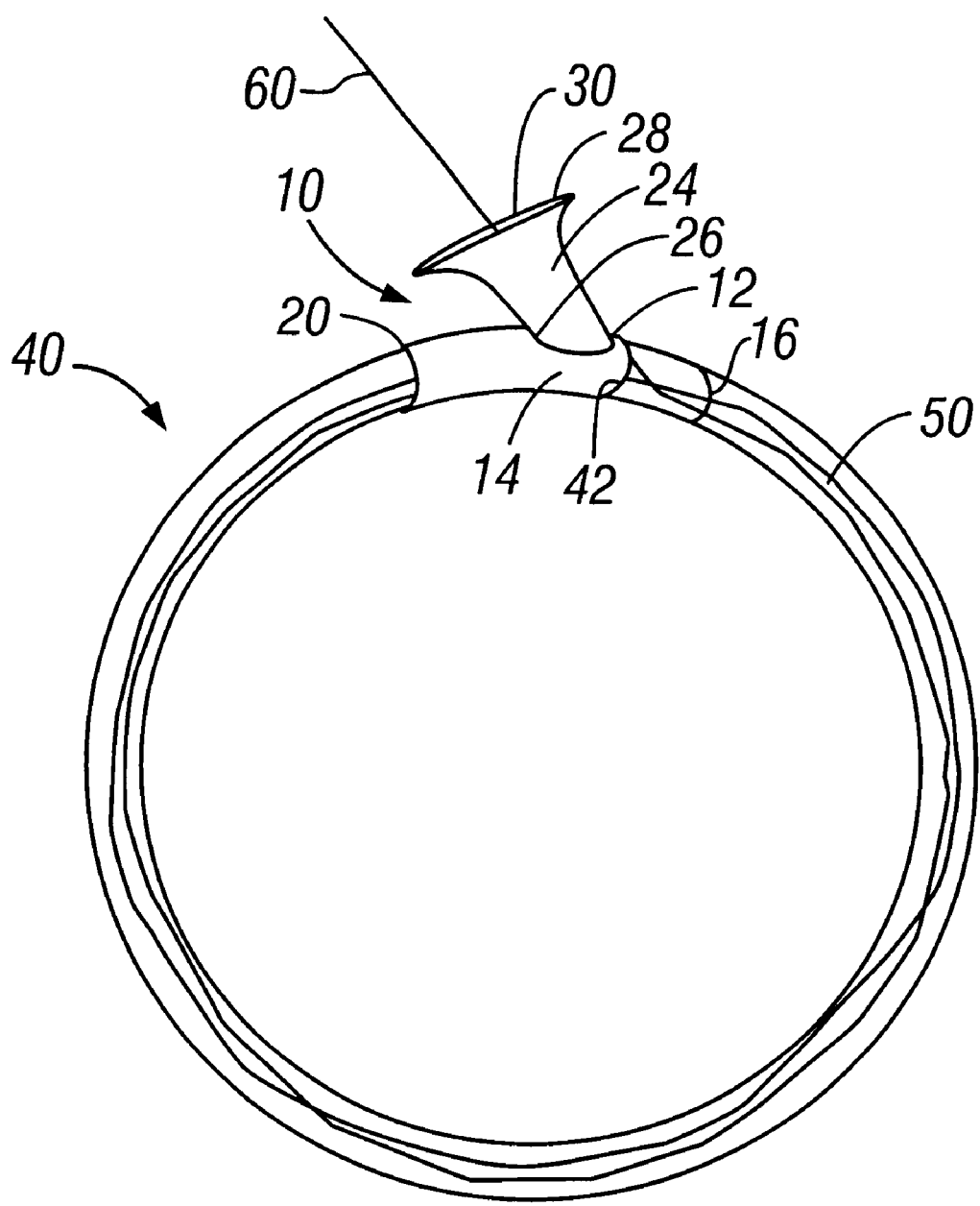
FIG. 3 is a perspective view of the converted hoop packing tube and adapter of FIG. 2 within which a medical guidewire is disposed.

FIG. 3 illustrates a medical guidewire 60 being inserted into the packaging tube 40 through the port 30 of enlarged end 28 of the funnel 24. The joining configuration of the adapter ends and the packaging tube ends prevents a medical guidewire from getting stuck on the junctions between the packaging tube 40 and the adapter 10 during insertion. After the guidewire is reinserted into the packaging tube, the adapter 10 may be removed, if desired, and the bridge connector may be reinserted to close the loop of the packaging tube.

Thus, the adapter 10 turns the packaging tube 40 into a storage tube by allowing medical guidewires to be reinserted into the packaging tube for storage and potential reuse. The adapter 10 may also be used with other packaging tubes, such as a flexible coil packing tube.

An alternative embodiment of the present invention would be to integrally form the tube and adapter of FIGS. 2 and 3 as a single piece. Such a device, for example, could be molded from a piece of plastic. The tube portion of the device could feature an enlarged passageway to accommodate several guidewires. Such a device could be sold absent guidewires as a storage device.

While the preferred embodiment of this invention has been shown and described, it will be apparent to those skilled in the art that changes and modifications may be made therein without departing from the spirit of the invention, the scope of which is defined by the appended claims.

What is claimed is:

1. An apparatus for storing medical guidewires, said apparatus comprising:
   a flexible tube with a leading end having a leading opening and a trailing end having a trailing opening; and
   an adapter comprising a conduit and a funnel, wherein said conduit includes a first end having a first opening, a second end having a second opening and a passage extending there between, and said funnel includes a port and a duct, where the duct is in communication with the passage of said conduit and the port,
   whereby the ends of said adapter are installed in said openings of the flexible tube to form a closed loop.

2. The apparatus of claim 1, wherein said funnel includes an enlarged end having the port formed therein.

3. The apparatus of claim 1, wherein the duct of said funnel extends at an angle from the passage of said conduit.

4. The apparatus of claim 1, wherein said second end of the conduit has a diameter larger than said first end of the conduit.

5. The apparatus of claim 1, wherein said first end of said conduit is inserted in said leading opening of said leading end of the flexible tube and said second opening of said second end of said conduit receives said trailing end of the flexible tube.

6. A method of storing medical guidewires comprising the steps of:
   a) providing a guidewire packaging tube with a leading end and a trailing end;
   b) providing an adapter having a conduit and a funnel, the conduit having a first end with a first opening and a second end with a second opening with a passage extending there between and the funnel in communication with the passage;
   c) connecting the first end of the adapter to the leading end of the packaging tube; and
   d) connecting the trailing end of the packaging tube to the second end of the adapter.

7. The method of claim 6, wherein step c) includes inserting the first end of the adapter into the leading end of the packaging tube and step d) includes inserting the trailing end of the packaging tube into the second opening at the second end of the adapter.

8. The method of claim 6, further comprising the step of:
   e) directing a guidewire through the funnel and the conduit passage into the packaging tube.

* * * * *